United States Patent
Yu

(10) Patent No.: US 9,551,675 B2
(45) Date of Patent: Jan. 24, 2017

(54) COMPUTED TOMOGRAPHY SYSTEM AND X-RAY COLLIMATOR THEREOF

(71) Applicant: Shenyang Neusoft Medical Systems Co., Ltd., Shenyang (CN)

(72) Inventor: Jun Yu, Shenyang (CN)

(73) Assignee: SHENYANG NEUSOFT MEDICAL SYSTEMS CO., LTD., Shenyang (CN)

(*) Notice: Subject to any disclaimer, the term of this patent is extended or adjusted under 35 U.S.C. 154(b) by 160 days.

(21) Appl. No.: 14/571,291

(22) Filed: Dec. 16, 2014

(65) Prior Publication Data

US 2015/0179291 A1 Jun. 25, 2015

(30) Foreign Application Priority Data

Dec. 19, 2013 (CN) .......................... 2013 1 0715096

(51) Int. Cl.
  *G01N 23/04* (2006.01)
  *G21K 1/04* (2006.01)
  *G21K 1/02* (2006.01)

(52) U.S. Cl.
  CPC ............. *G01N 23/046* (2013.01); *G21K 1/025* (2013.01); *G01N 2223/316* (2013.01)

(58) Field of Classification Search
  CPC ............ G21K 1/025; G21K 1/02; A61B 6/032
  See application file for complete search history.

(56) References Cited

U.S. PATENT DOCUMENTS

| 5,804,046 A | 9/1998 | Sawada et al. |
| 2002/0015474 A1 | 2/2002 | Tybinkowski et al. |
| 2007/0258566 A1 | 11/2007 | Eckenbach |
| 2013/0070892 A1* | 3/2013 | Mori ....................... A61B 6/032 378/7 |
| 2013/0322603 A1* | 12/2013 | Kurochi ................. G21K 1/025 378/147 |

FOREIGN PATENT DOCUMENTS

| CN | 1409326 A | 4/2003 |
| CN | 1791944 A | 6/2006 |

(Continued)

OTHER PUBLICATIONS

The First Office Action dated Jul. 3, 2015 regarding the Chinese priority patent application (201310715096.5).

*Primary Examiner* — Hoon Song
(74) *Attorney, Agent, or Firm* — Kilpatrick Townsend & Stockton LLP

(57) ABSTRACT

A computed tomography system and an X-ray collimator thereof are provided, which have a good collimator effect. The X-ray collimator includes a plurality of first plates extending in the circumferential direction of the computed tomography system and a plurality of second plates extending in the axial direction of the computed tomography system. The first plates and the second plates are inserted and engaged. Two adjacent first plates and two adjacent second plates define a through hole, and the extensions of the side walls of the through hole intersect at the focal spot of an X-ray source, so that the X-rays can pass through the through hole in a straight line. Since the extensions of the side walls of the through holes intersect at the focal spot of the X-ray source, the through holes are aligned with the radiation direction of corresponding X-rays.

8 Claims, 16 Drawing Sheets

(56) References Cited

FOREIGN PATENT DOCUMENTS

| | | |
|---|---|---|
| CN | 101221824 A | 7/2008 |
| CN | 102525526 A | 7/2012 |
| CN | 102670235 A | 9/2012 |
| CN | 103310867 A | 9/2013 |
| CN | 103445802 A | 12/2013 |
| EP | 1045398 A2 | 10/2000 |

* cited by examiner

COMPUTED TOMOGRAPHY SYSTEM AND X-RAY COLLIMATOR THEREOF

This application claims the priority to Chinese Patent Application No. 201310715096.5 titled "COMPUTED TOMOGRAPHY SYSTEM AND X-RAY COLLIMATOR THEREOF", filed with the Chinese State Intellectual Property Office on Dec. 19, 2013, the entire disclosure of which is incorporated herein by reference.

TECHNICAL FIELD

The present application relates to the technical field of medical machinery, and particularly to an X-ray collimator of a computed tomography system. The present application also relates to a computed tomography system having the X-ray collimator.

BACKGROUND

In the computed tomography (CT) system, X-rays, which are radiated from the focal spot of an X-ray resource like a point, pass through a subject to be checked. After penetrating the subject, the X-rays are attenuated in two-dimensional distribution and measured by a detector, and then its distributed data are processed by a computer to generate a corresponding tomography image.

In the current medical computed tomography system, a solid detector is mainly used for X-ray measurement. Such a solid detector is often an array of an X-ray photoelectric receivers, for example, 16×16 or 16×32 pixel matrix, formed by arranging a plurality of photoelectric semiconductor units in a grid matrix.

In the ideal condition, an X-ray travels in a straight line. The data that shall be collected on each pixel of an X-ray detector correspond to the attenuation of the X-rays which penetrate the subject to be checked in the straight path from the focal spot to this pixel. The X-ray that is radiated from the focal spot to the X-ray detector in a straight line is referred to as a primary ray.

In the practical use, when an X-ray emanated from the focal spot passes through the subject to be checked to a surface of the detector, it is inevitable that the X-ray interacts with the subject so that the primary ray is scattered to form a scattered ray referred to as a secondary ray. The secondary ray formed by scattering travels in a path deviated from its original straight path and radiates on a surface of a pixel in the vicinity of the original pixel. Finally, besides the primary rays, the X-rays detected by each pixel of the detector further include the scattered secondary rays.

It can be known from the principle of formation of the secondary ray that a noise source may certainly be formed as a result of the secondary rays blending with the primary rays traveling in straight lines, causing reduction of the recognition capability of the detector on small difference of the contrast and decrease of the density resolution of the image system. Thus, it is a technical problem to be solved presently for those skilled in the art to reduce the scattered rays reaching the detector.

To solve the above technical problem, an X-ray collimator is often placed between the subject to be checked and the detector for reducing the influence of the scattered rays on the image density resolution.

Reference is made to FIG. 1, which is a schematic view of a conventional CT scanner having an X-ray collimator in the prior art.

A conventional X-ray collimator consists of a structure array which can absorb X-rays and is similar to the array of detector. A Chinese patent application No. 03826552.4 discloses an anti-scattered X-ray collimator of a CT scanning device. As shown in FIG. 1, the CT scanning device includes an X-ray source 2', which may generate a conical X-ray beam 1' indicated by dash lines in a controllable way, and an array 4' of the X-ray detector 3'. The conical X-ray beam 1' radiates from the focal spot 21' of the X-ray source 2'. The array 4' includes rows 31' and columns 32' of the X-ray detector 3', wherein the rows 31' are orthogonal or approximately orthogonal to the scanning center axis of the scanning device, and the columns 32' are parallel or approximately parallel to the scanning center axis. The X-ray detector 3' in the array 4' is shielded by a two-dimensional X-ray collimator 5'. The X-ray collimator 5' in FIG. 1 is partially cut away to illustrate the X-ray detector 3'. The X-ray collimator 5' includes "row" slices 51' positioned between the rows 31' of the X-ray collimator 3', and "column" slices 52' positioned between the columns 32' of the detector 3'. The "row" slices 51' and "column" slices 52' can be positioned such that their respective planes substantially intersect at the focal spot 21'.

With the above X-ray collimator 5', the "raw" slices 51' and "column" slices 52' define and form a plurality of through holes or through gaps whose side walls are oriented in line with the straight paths from the focal spot 21' to the surface of the X-ray detector 3'. That is to say, the extensions of the side walls of the plurality of through holes or through gaps intersect at the focal spot 21'. In this way, the area of the X-ray detector 3' shielded by the side walls of the through holes or through gaps is smallest, i.e., the primary ray is shielded minimally, so that the primary rays may pass through the through holes or through gaps to the X-ray detector 3' with least attenuation, thereby ensuring a high efficiency of the X-ray detector 3'.

As can be known from the above operating principle of the X-ray collimator 5', there is a need for the X-ray collimator 5' to absorb the scattered rays as many as possible on the one hand and to make most of the primary rays reach the surface of the X-ray detector 3' with least attenuation on the other hand. The above requirement can be met by adjusting the height of the X-ray collimator 5', the thickness of the walls of each through hole, and the shape of each through hole. And, it also has a high requirement for the size precision of each through hole in the X-ray collimator 5'. If the through holes cannot align with the pixel units of the X-ray detector 3', on the one hand, the effective primary rays may be shielded, causing decrease of the detecting efficiency, and on the other hand, the non-uniform of the units may cause the image distortion. Therefore, the X-ray collimator 5' plays an important role on a high-quality image scanned through a computed tomography system.

The current X-ray collimator as shown in FIG. 1 may be made by a first method in which sheet metal is stamped to form bended grid members and the grid members are adhered to each other, referring to the Chinese patent application No. 03826552.4 titled "Anti-scattered X-ray collimator of a CT scanning device" for further details. However, the collimator formed by the first method has a low precision due to springback during stamping. The X-ray collimator as shown in FIG. 1 can be made by a second method in which the slices with an array of grids are stacked, referring to the Chinese patent application No. 200810009502.5 titled "stacked CT collimator and the manufacturing method thereof" for further details. However, the stacked structure of multiple slices formed by the second method is complicate, and it is difficult to ensure uniformity of anti-scattering since the regions of slices where the primary rays pass through are required to have uniform sizes. The X-ray collimator can be made by a third method similar to 3D printing, referring to the Chinese patent applicant No. 02144468.4 titled "method of manufacturing scatting grid or collimator" for further details. However, the wall thickness of the through holes formed by printing in the third method may be thicker so as to greatly shield the primary rays, and may be non-uniform so as to cause non-uniformity of anti-scatting effect. The X-ray collimator may be formed by a fourth method of tenon connection, referring to the U.S. patent application with publication No. 20070258566A1 titled "ANTI-SCATTER-GRID" for further details. However, the X-ray collimator formed by the fourth method has a large number of components, causing the complicate assembling process.

Therefore, it is a technical problem to be solved presently for those skilled in the art to design an X-ray collimator of computed tomography system having an improved collimation effect and a simple structure.

SUMMARY

An object of the present application is to provide an X-ray collimator of a computed tomography system having a simple structure and a good collimation effect.

Another object of the present application is to provide a computed tomography system having the X-ray collimator, which has a high detecting precision.

To solve the above problems, there is provided in the present application an X-ray collimator of a computed tomography system, including a plurality of first plates extending in the circumferential direction of the computed tomography system and a plurality of second plates extending in the axial direction of the computed tomography system. The first plates and the second plates are inserted and engaged with each other, and two adjacent first plates and two adjacent second plates define a through hole. The extensions of the side walls of each through hole intersect at the focal spot of the X-ray source, making the X-ray pass through the through hole in a straight line.

The X-ray collimator of the present application is formed by a plurality of first plates and second plates inserted and engaged with each other, and adjacent first plates and adjacent second plates define a plurality of through holes. The extensions of the side walls of each through hole intersect at the focal spot of the X-ray source, which ensures the through hole to extend in the radiation direction of the corresponding X-rays. Thus, an X-ray radiating from the focal spot of the X-ray source can pass through the through hole in a straight line, and finally reach a detecting unit of the X-ray detector without any shielding while having a good collimation effect. Furthermore, the side walls of the through hole may absorb and block the scattered rays, which would otherwise interfere with the X-rays in the through hole, thereby improving the anti-scattering effect and increasing the detecting precision. The assembling process of the X-ray collimator of the present application can be completed simply by inserting and engaging the first plates and the second plates with each other. Thus, the structure of the X-ray collimator is simple and the manufacturing and assembling process thereof is simple.

Preferably, each of the first plates has a plurality of first slits spaced apart in the circumferential direction, and each of the second plates is positioned and inserted in the corresponding first slit.

The first slits may be provided only in the first plate. Then, the second plate is inserted in the first slit, so that the structure is simplified and the assembling efficiency is improved.

Preferably, the first slit extends from top towards bottom and does not run through the lower end face of the first plates, and the second plate is provided at its lower end with a plurality of second slits extending from bottom towards top. The first slits are engaged with the middle-upper portions of the second plates, and the second slits are engaged with the lower ends of the first plates.

The first slits may also be partial-through slits, and a solid portion is left at the lower end of the first plate. The second plate is provided with a plurality of second slits for engaged with the solid portion. Thus, the middle-upper portion of the second plate is engaged with the first slit, and the second slit is engaged with the lower end of the first plate, so that the first plates and the second plates can be positioned reliably so as to define the structures of the through holes.

Preferably, the first slit is provided in the middle of the first plate, and its height is not smaller than the height of the second plate, so that the entire second plate is inserted into the first slit in the axial direction.

The first slits may also be provided in the middle of the first plate, and the entire second plate may be inserted into the first slits, so that the structure of the first plates and second plates is further simplified and the assembling convenience is improved.

Preferably, the upper end face and the lower end face of the second plate are fixed with the upper end face and the lower end face of the first slit by adhesive bonding or welding.

Preferably, the upper end of the second plate is provided with second upper slits extending from top to bottom, so that the second upper slits receive and are engaged with the upper ends of the first plates.

Additionally or alternatively, the lower end of the second plate is provided with second lower slits extending from bottom to top, so that the second lower slits receive and are engaged with the lower ends of the first plates.

When the second plate is inserted into the first slit in its entirety, because the first slits are arranged in the middle of the first plate, the upper end and the lower end of the first plate are solid portions. The upper end and/or lower end of the second plate may further be provided with slits, thereby achieving an engagement of the first plates and the second plates at their upper and lower ends and improving the reliability of positioning.

Preferably, the second plate may include two or more sub-plates stacked in a vertical direction. The second upper slits are provided in the top sub-plate and the second lower slits are provided in the bottom sub-plate. The second plate may further include an infill plate which could press and position the sub-plates in the first slit.

The second plate may include a plurality of sub-plates stacked in a vertical direction. Then, each of the sub-plates could be pressed and positioned in the first slit by the infill plate, thereby improving the reliability of positioning.

Preferably, the first slit may include a first upper slit at upper end and a second lower slit at lower end. The second plate may include an upper plate engaged and positioned in the first upper slit and a lower plate engaged and positioned in the first lower slit.

When the first slit includes the first upper slit and the first lower slit, the second plate may include an upper plate and a lower plate. Then, the upper plate may be engaged with the first upper slit, and the lower plate may be engaged with the first lower slit, which not only improves the positioning reliability of the first plate and the second plate, but also avoids a deformation since the second plate is too high. Therefore, it ensures the orientation of through hole to be identical with the radiation direction of the corresponding X-ray, and the collimation effect is improved.

Preferably, the lower end of the upper plate has a plurality of upper plate slits extending in from bottom to top, and the upper plate slits are engaged with the lower end of the first upper slit.

Additionally or alternatively, the lower end of the lower plate has lower plate slits extending from bottom to top, and the lower plate slits are engaged with the lower end of the first lower slit.

Accordingly, the lower ends of the upper plate and the lower plate may be provided with slits, thereby achieving a crossing connection with the upper slit and the lower slit of the first plate, and improving the positioning reliability.

Preferably, it further includes a positioning plate, which has a plurality of positioning grooves extending in the circumferential direction, and each of the positioning grooves is engaged with and positioned relative to the upper end of the corresponding first plate.

The positioning plate functions to a positioning tool for the first plate, and is provided with a corresponding positioning groove for mounting each of the first plates. Then, the upper end of each first plate is inserted and positioned in the positioning groove, thereby mounting the first plate precisely and quickly. Also, the positioning plate may serves as a cover plate, which covers the top of the first plates and closes the entire the X-ray collimator, preventing foreign matters such as dust from falling into the collimator.

Preferably, the positioning groove is a run-through groove.

Preferably, the positioning groove includes two or more sub-grooves spaced apart in the circumferential direction. The solid portion between the adjacent sub-grooves is set to have a predetermined width. The upper end of each of the first plates is provided with cutout notch for accommodating the solid portion.

The positioning groove may include a plurality of sub-grooves. Then, the entire positioning plate can have a good rigidity. Compared with a long groove in the circumferential direction, the plurality of sub-grooves may avoid the positioning plate from bending to cause reduction of precision. Although it needs to provide cutout notch for accommodating the corresponding solid portion at the upper end of the first plate, the size of the notch is much smaller than the height of the first plate, which hardly influences the structure of the through hole.

Preferably, a first guard plate is provided at each of two ends of the first plate, and a second guard plate is provided at each of two ends of the second plate. The first guard plates 5 and the second guard plates 6 enclose the ends of the first plates and the second plates.

Preferably, the thickness of the first guard plate is substantially half of the thickness of the second plate, and the thickness of the second guard plate is substantially half of the thickness of the first plate.

The thickness of the first guard plate and the second guard plate may be set. When the adjacent X-ray collimators are joined, the two first guard plates are joined and serve as a second plate engaged with the first plate. The two second guard plates are joined and serve as a first plate engaged with the second plate. Two adjacent X-ray collimators may be joined to form a large X-ray collimator, which can be joined with more X-ray collimators.

There is further provided in the present application a computed tomography system, including an X-ray detector and an X-ray collimator for collimating the X-rays radiating to the X-ray detector. The X-ray collimator is one of the above X-ray collimators.

Preferably, the X-ray collimator is mounted on the X-ray detector, and each through hole corresponds to a detecting unit of the X-ray detector. A plurality of partition grooves are provided in partition regions between pixels of the X-ray detector, and the lower ends of the first plates are embedded into the partition grooves.

Because the computed tomography system of the present application includes one of the above mentioned X-ray collimators, the computed tomography system may produce the same technical effects generated by the X-ray collimator computed tomography system, which is not described here any more.

BRIEF DESCRIPTION OF THE DRAWINGS

In FIG. 1:

| 1' | conical X-ray beam; | 2' | X-ray source; |
|---|---|---|---|
| 21' | focal spot; | 3' | X-ray detector; |
| 31' | row; | 32' | column; |
| 4' | array; | 5' | X-ray collimator; |
| 51' | "row" slice; | 52 | "column" slice; |

In FIGS. 2-17:

| 1 | first plate; | 11 | first slit; |
|---|---|---|---|
| 12 | first upper slit; | 13 | first lower slit; |
| 14 | notch; | 2 | second plate; |
| 21 | second slit; | 22 | second upper slit; |
| 23 | second lower slit; | 24 | sub-plate; |
| 25 | infill plate; | 26 | upper plate; |
| 261 | slit of upper plate; | 27 | lower plate; |
| 271 | slit of lower plate; | 3 | through hole; |
| 4 | positioning plate; | 41 | positioning groove; |
| 411 | sub-groove; | 5 | first guard plate; |
| 6 | second guard plate; | 7 | X-ray detector; |
| 8 | X-ray collimator. | | |

DETAILED DESCRIPTION

An X-ray collimator of a computed tomography system is provided according to an aspect of the present application. The X-ray collimator has a simple structure and a good collimation effect.

A computed tomography system having the X-ray collimator is provided according to another aspect of the present application. The computed tomography system has a high detecting precision.

For those skilled in the art to better understand technical solutions of the present application, the present application will be described in detail in conjunction with drawings and embodiments hereinafter.

Figure 1:
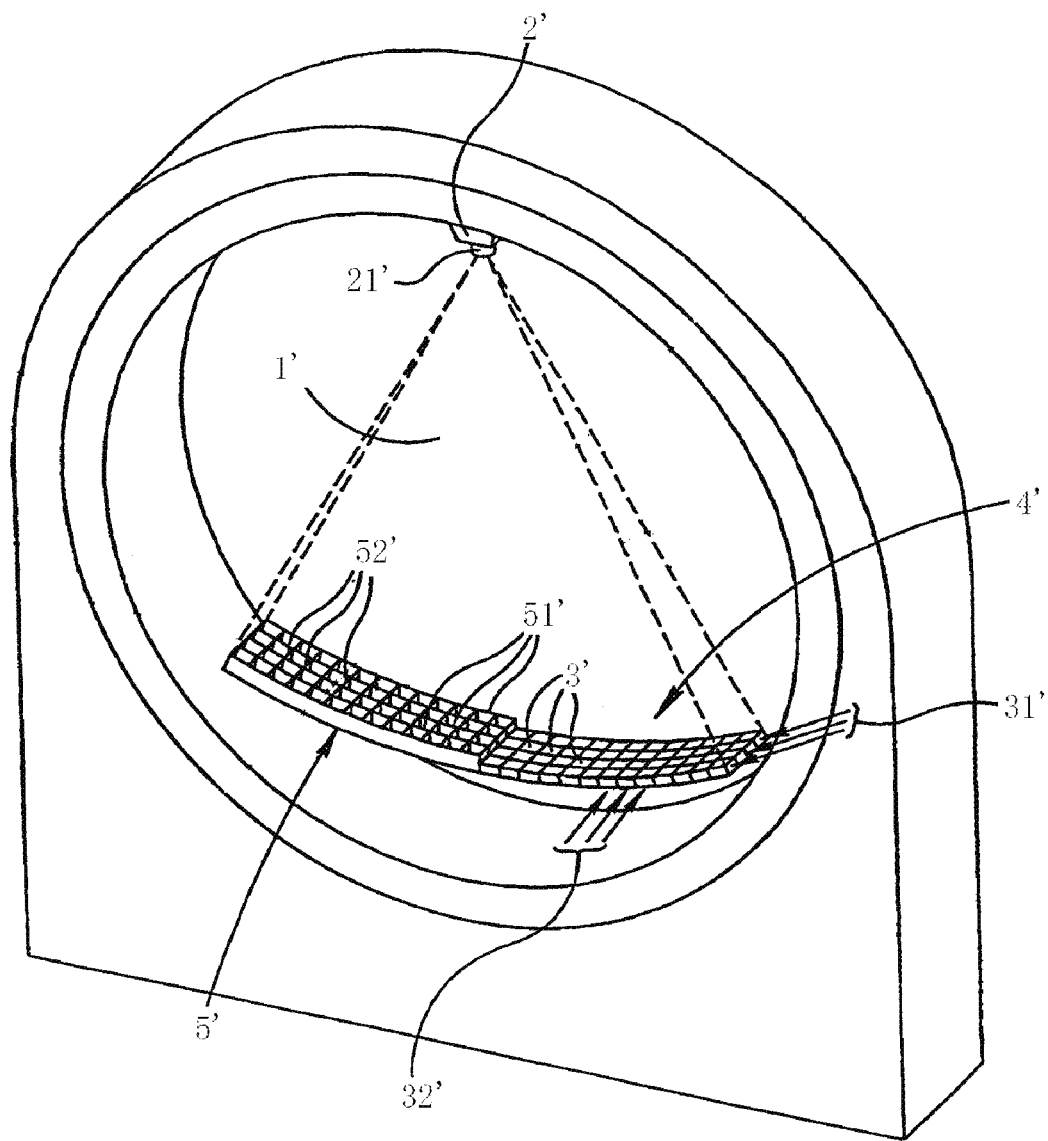
FIG. 1 is a schematic view of a conventional CT scanning devices having an X-ray collimator in the prior art.
Figure 2:
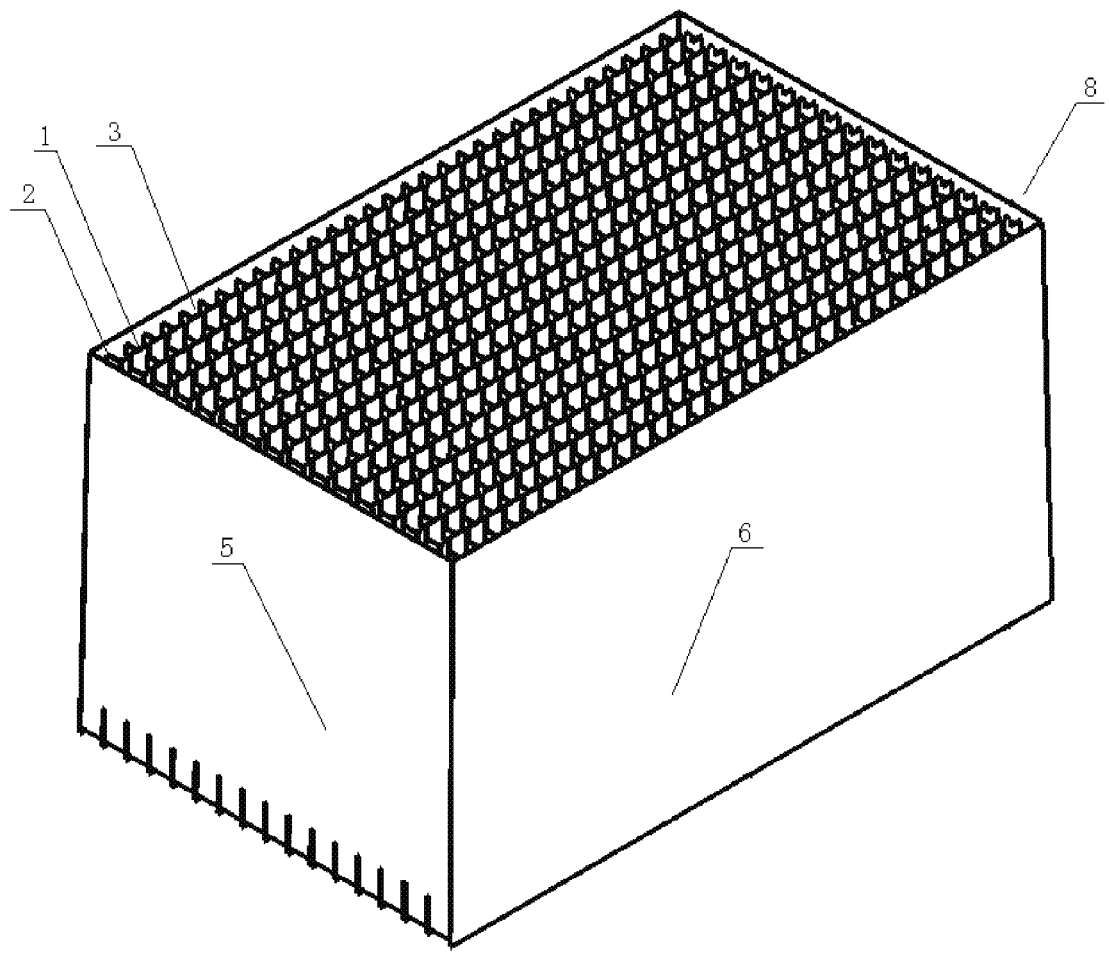
FIG. 2 is a schematic structural perspective view of the X-ray collimator according to one embodiment of the present application.
Figure 16:
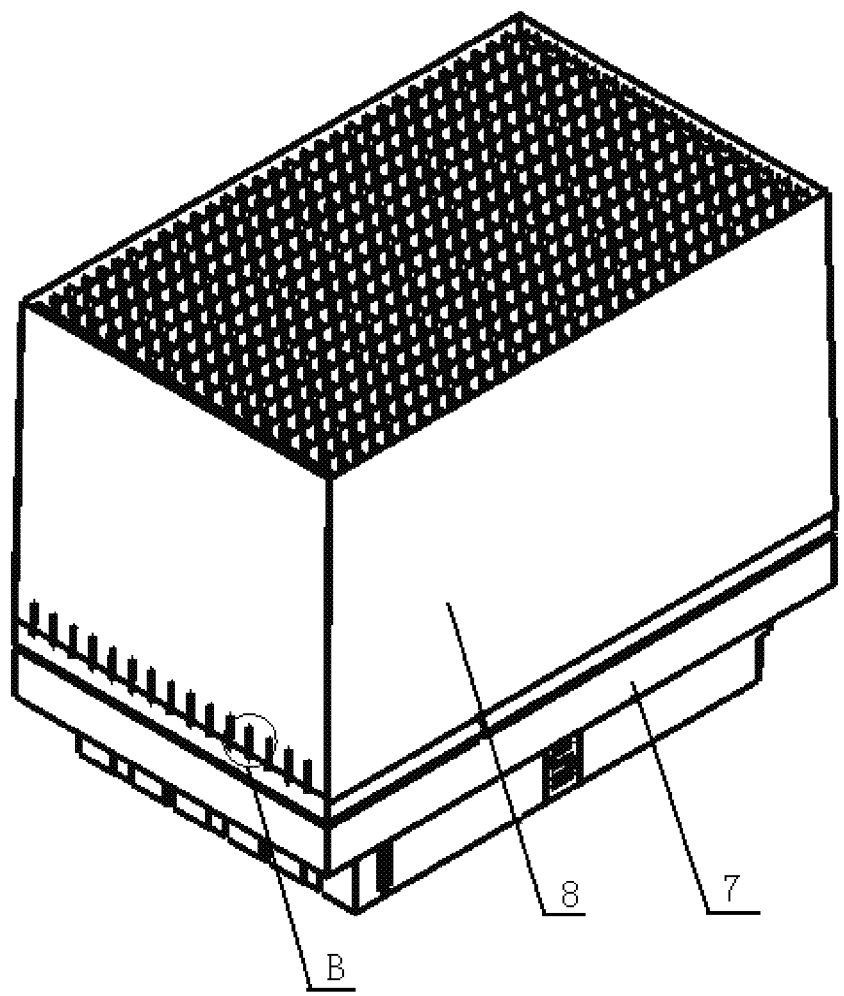
FIG. 16 is a schematic structural perspective view of the X-ray collimator in FIG. 2 mounted on an X-ray detector.

Referring to FIGS. 2 and 16, FIG. 2 is a schematic structural perspective view of the X-ray collimator according to one embodiment of the present application; and FIG. 16 is a schematic structural perspective view of the X-ray collimator in FIG. 2 mounted on an X-ray detector.

The X-ray collimator 8 in the present application includes a plurality of first plates 1 and a plurality of second plates 2. The first plates 1 each extend in the circumferential direction of the computed tomography system, and the second plates 2 each extend in the axial direction of the computed tomography system. The first plates 1 and the second plates 2 are crossed and engaged. Two adjacent first plates 1 and two adjacent second plates 2 define and form a plurality of through holes 3. The extensions of side walls of the through holes 3 intersect at the focal spot of the X-ray source, i.e., the extension planes of the first plates 1 and the second plates 2 intersect at the focal spot of the X-ray source. Then, the X-rays radiating from the focal spot of the X-ray source may pass through the corresponding through hole 3 in a straight line without shielding, and further be effectively received by the X-ray detector 7. The side walls of the through holes 3 also can shield the scattered rays when the X-rays penetrate the subject to be checked, which would otherwise adversely affect the detecting result.

Though the X-ray collimator in the present application includes a plurality of the first plates 1 and a plurality of the second plates 2, it will be appreciated that the number of the first plates 1 may be not equal to that of the second plates 2. That is to say, the term "plurality of" as mentioned herein refers to an uncertain number.

The circumferential direction and the axial direction herein are defined with reference to the entire computed tomography system, wherein the axial direction refers to a direction parallel to the scanning central axis of the computed tomography system, and the circumferential direction refers to a rotation direction of the computed tomography system during scanning.

The first plate 1 extending in the circumferential direction of the computed tomography system means that the first plate 1 may substantially extend in the circumferential direction of the computed tomography system with a deviation from the circumferential direction of the computed tomography system by an angle, generally a small deviation. The second plate 2 extending in the axial direction of the computed tomography system means that the second plate 2 may substantially extend in the axial direction of the computed tomography system with a deviation from the axial direction by an angle, generally a small deviation.

The first plates 1 and the second plates 2 both may be configured as curved plates, flat plates or other regularly-shaped plates, depending on the requirements of mounting of the X-ray detector 7 and the structure of the through hole 3 to be formed.

For collimating the X-ray, the through holes 3 each shall be oriented in accordance with the radiation direction of the X-ray, i.e. the extensions of all of the side walls (faces of the first plates 1 and the second plates 2) of the through hole 3 intersect at the focal spot of the X-ray source. The X-ray detector 8 of the present application may be in a sector region of a sphere having a center at the focal spot of the X-ray source and a radius from the focal spot to the detecting unit of the X-ray detector 7. Generally, the X-ray collimator 8 is in a frustum shape. Since the through hole 3 functions as the passage of the X-rays, and the X-rays each are emanated from the focal spot of the X-ray source to the X-ray detector 7, the space of the through hole close to the X-ray source is relatively small. Thus, the size of through hole 3 may gradually increase in the incidence direction of the X-ray, such that the through hole 3 has a sufficient space at a side approximate to the X-ray source in order to facilitate a precise incidence of the X-ray and can, at a side approximate to the X-ray detector 7, be matched with the detecting unit of the X-ray detector 7 perfectly.

Compared with the conventional X-ray collimator, the X-ray collimator 8 of the present application uses the first plates 1 and the second plates 2 crossed and engaged with each other to form a plurality of through holes 3. The X-ray collimator 8 may be easily assembled, only by determining orientations of the first plates 1 and the second plates 2 to define the structure of each through hole 3 such that the orientation of the through hole 3 is aligned with the incidence direction of the X-rays, thereby allowing the X-rays to pass through the through hole 3 in a straight line to the detecting unit of the X-ray detector 7 without blocking the X-rays while effectively absorbing or blocking the scattered rays. Accordingly, the X-ray collimator 8 has a good collimation effect.

To effectively absorb the scattered rays, the first plates 1 and the second plates 2 may be made of material with high X-ray attenuation, for example, W (tungsten), Mo (molybdenum), Pb (lead), Ta (tantalum), or any alloy thereof. Generally, the thickness of the first plate 1 and the second plate 2 is set between 0.01 mm~0.3 mm for blocking the X-rays minimally while effectively shielding the scattered rays.

In theory, it would be better to have the overall height of the X-ray collimator 8 higher. However, considering the mounting space and manufacturing process and so on, the height may be set to be 5~50 times of the side length of each pixel, usually 5 mm~50 mm.

It is noted that the height herein means the size of the first plate 1 and the second plate 2 in the incidence direction of the X-ray. The X-ray herein means a primary ray radiating from the focal spot to the X-ray detector 7 in a straight line, and the scattered ray herein means a secondary ray formed by scattering during the process of X-rays penetrating the subject to be checked, unless otherwise stated.

A further modification may be made to the X-ray detector of the present application.

Figure 3:
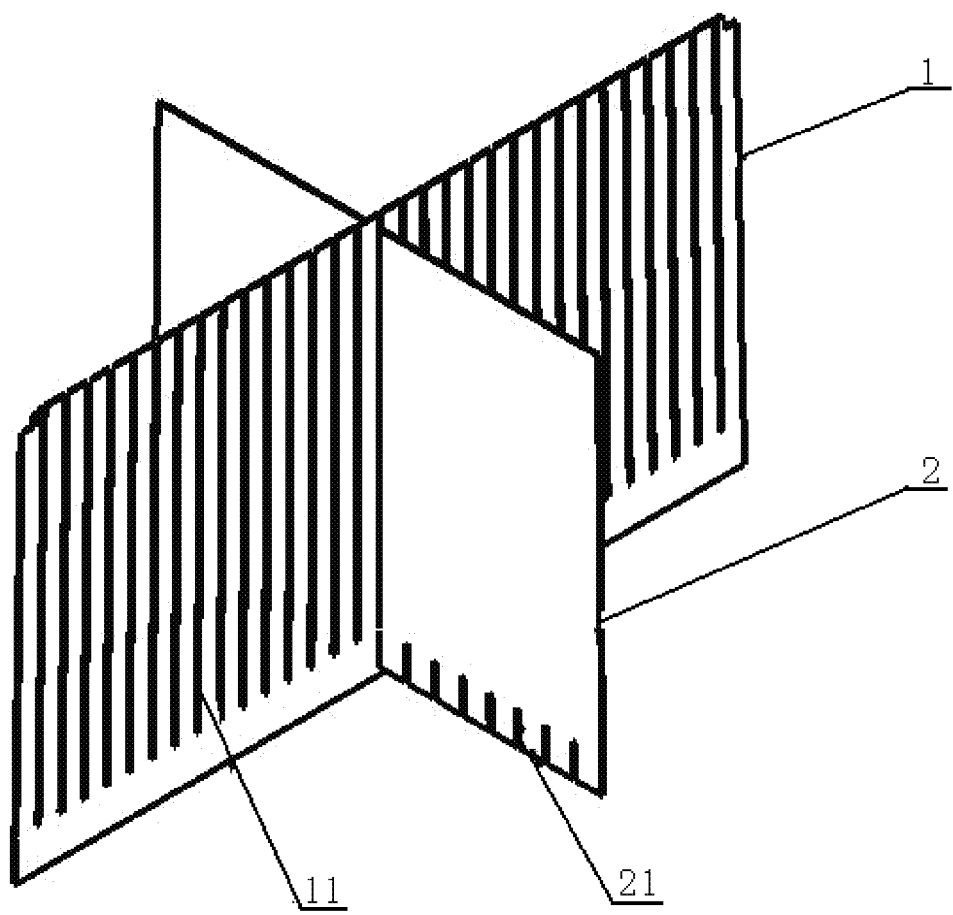
FIG. 3 is a schematic structural perspective view of a first plate and a second plate engaged in a first crossing connection according to the present application.
Figure 4:
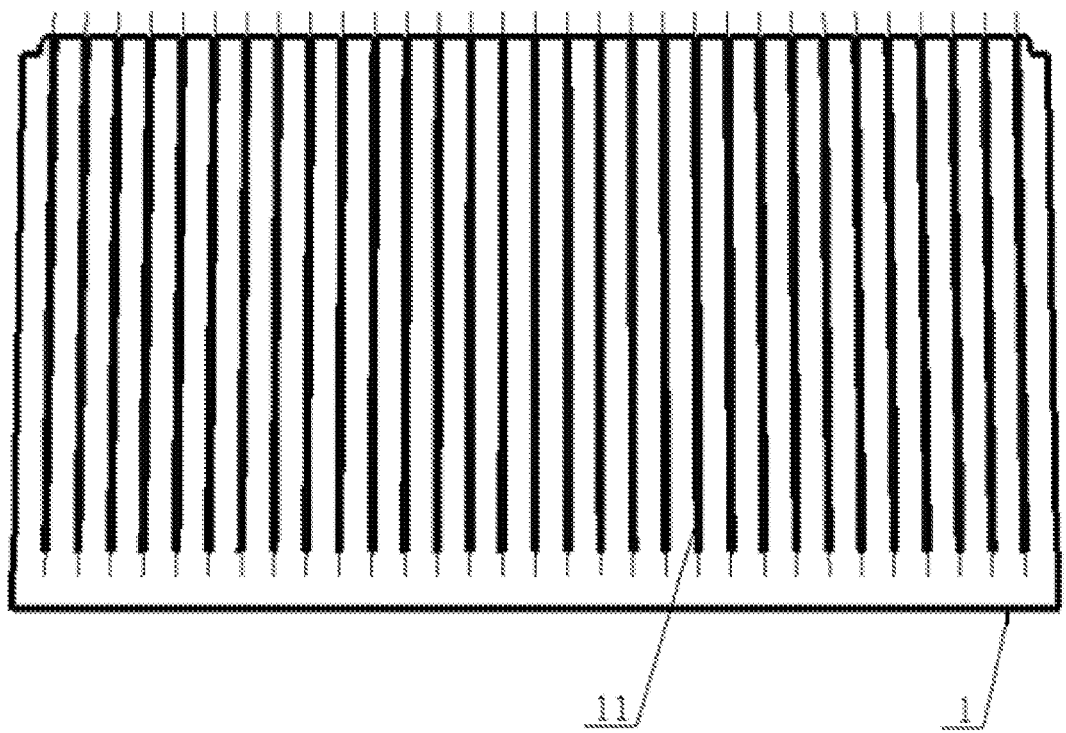
FIG. 4 is a front structural schematic view of the first plate shown in FIG. 3.
Figure 5:
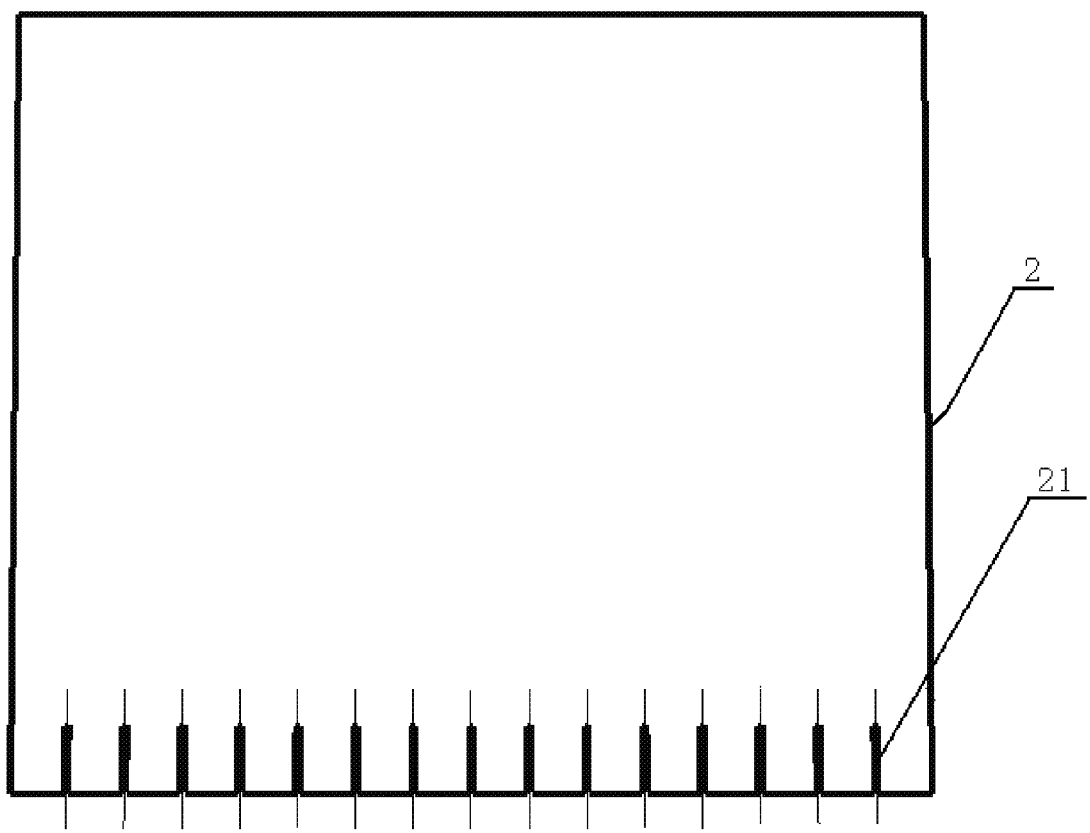
FIG. 5 is a front structural schematic view of the second plate shown in FIG. 3.

Referring to FIGS. 3 to 5, FIG. 3 is a schematic structural perspective view of a first plate and a second plate engaged in a first crossing connection according to the present application; FIG. 4 is a front structural schematic view of the first plate shown in FIG. 3; and FIG. 5 is a front structural schematic view of the second plate shown in FIG. 3.

In a first embodiment, the first plate 1 may be provided with a plurality of first slits 11, which are spaced apart in the extension direction of the first plate 1, such that the second plates 2 can be inserted and positioned in the respective first slits 11.

The first plates 1 each may be provided with the first slits 11, and then the second plate 2 is sequentially engaged with the first plates 1. The second plates 2 may be inserted in the first plates 1, with the second plates 2 being spaced apart in the extension direction of the first plates 1, thereby dividing the space defined by the first plates 1 and the second plates 2 into a plurality of grids to form a plurality of through holes 3. By providing the first slits 11 in the first plate 1, it is not only simple in structure but also may receive the second plates 2 with ease, thereby improving the reliability of the positioning and assembly convenience.

Similarly, those skilled in the art should appreciate that the second plate 2 may be provided with the silts, so as to insert the first plates 1 into the second plate 2; or that the first plates 1 and the second plates 2 both may be provided with the silts, so as to interlace them with each other.

As shown in FIGS. 3 and 4, the first silt 11 may extend from top to bottom, but does not run through the lower end face of the first plate 1, i.e., the lower end of the first slit 11 is at a distance from the lower end face of the first plate 1, and the portion of the first plate 1 within this distance is solid. The lower end of second plate 2 may be provided with the second slits 21, which may extend from bottom to top. The second plate 2 may be engaged into the first slit 11 from top to bottom, and positioned in the first plate 1 after the middle-upper portion of the second plate 2 is inserted in the first slit 11. When the second slit 21 of the second plate 2 is moved to the lower end of the first slit 11, the second plate 2 continues to go downwards, and as a result, the second slit 21 of the second plate 2 receives and is engaged with the solid portion of the lower end of the first plate 1, as shown in FIG. 3. Thus, the first plate 1 and the second plate 2 are positioned and engaged with each other reliably.

The middle-upper portion of the second plate 2 refers to a portion except for the second slit 21 in a vertical direction, i.e., the solid portion of the second plate 2.

The term "inserted and engaged" or the like as used herein means that both of the two parts to be engaged are provided with slits, and the two parts are engaged with each other through their slits oppositely, i.e., the two parts are inserted and engaged with each other through the slits aligned with each other. The term "positioned and engaged" means that at least one of the parts to be connected is provided with slits, so as to receive and is fitted with another part to be connected, thereby positioning and engaging the two parts with each other. Apparently, the case of "positioned and engaged" includes the case of "inserted and engaged".

In addition, the solid portion mentioned herein means a solid portion where a structure such as a slit does not run through.

The first slit 11 may be in transition or clearance fit with the second plate 2, and the second slit 21 may be in transition or clearance fit with the first plate 1, which is applicable to any inserted or engaged part as mentioned herein and will not be described below.

To further improve the reliability of positioning of the first plates 1 and the second plates 2, an adhesive (e.g., 502 glue or the like) with low X-ray attenuation may be used to bond and position the cross joints of the first slits 11 and the second slits 21. Alternatively, the first plates 1 and the second plates 2 may be welded at the cross joints of the first slits 11 and the second slits 21.

In any structure using adhesive for positioning as will be described below, the adhesive may be replaced by welding. And, the adhesive used in the bonding refers to an adhesive with a low X-ray attenuation.

The transmission direction of the X-ray is defined as a vertical direction. Thus, the "upper or top" part refers to be proximate to the focal spot, and the "lower or bottom" part refers to be proximate towards the X-ray detector 7.

Because the X-rays are radiated from the focal spot, each X-ray may define its own vertical direction which is not a uniquely determined direction. That is to say, the extension directions of the first slits 11 and the second slits 21 depend on the orientations of the through holes 3. The first slits 11 extend in different directions, and the second slits 21 extend in different directions.

For facilitating the crossing connection, the first slits 11 may extend from the upper end face of the first plate 1 towards the bottom, i.e., the upper end of the first plate 1 is open. The second slits 21 may extend from the lower end face of the second plate 2 towards the top, i.e., the lower end of the second plate 2 is open. Considering the stability of insertion, the height of the first slit 11 should be larger than half of the entire height of the first plate 1, as shown in FIG. 4. In order to avoid the interference between the first slits 11 and the second slits 21 in the insertion process, which may otherwise cause a distortion of the first plates 1 and the second plates 2 and even an impracticable insertion, the height of the second slit 21 should not be too high, usually lower than 5 mm, as show in FIG. 5. That is to say, the first slit 11 is set to be a long slit, and the second slit 21 is set to be a short slit. Similarly, when the first plate 1 is inserted in the second plate 2, the first slit 11 may be set to be a short slit, and the second slit 21 may be set to be a long slit.

Unless otherwise particularly stated, the slit that does not run through the plate herein is the long slit, and the slit that is arranged at one end (upper end or lower end) of the first plate 1 or the second plate 2 is often the short slit.

In addition, because the height of the second slit 21 is short, and only the lower end of the first plate 1 is inserted in the second slit 21, the second slit 21 may be oriented not to point towards the focal spot, but to be parallel to each other, which can simplify the manufacturing process without influencing the positioning precision of the first plate 1.

Considering that only the lower end of the first plate 1 is positioned in the second slits 21, an assembling tool having a plurality of parallel positioning grooves can be used for achieving the assistant positioning and assembling of the upper end of the first plate 1 during assembly.

Figure 6:
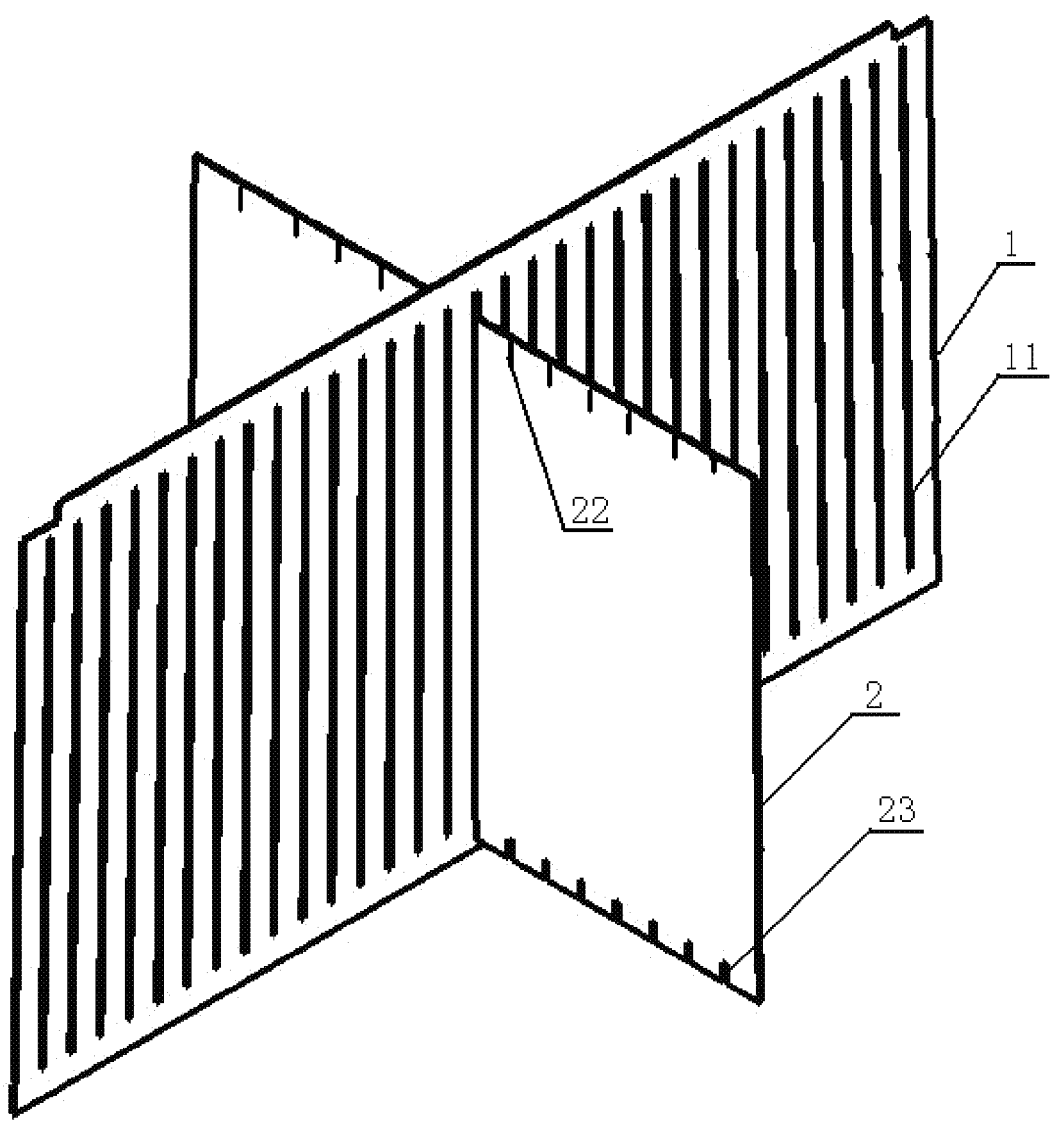
FIG. 6 is a schematic structural perspective view of a first plate and a second plate engaged in second crossing connection according to the present application.
Figure 7:
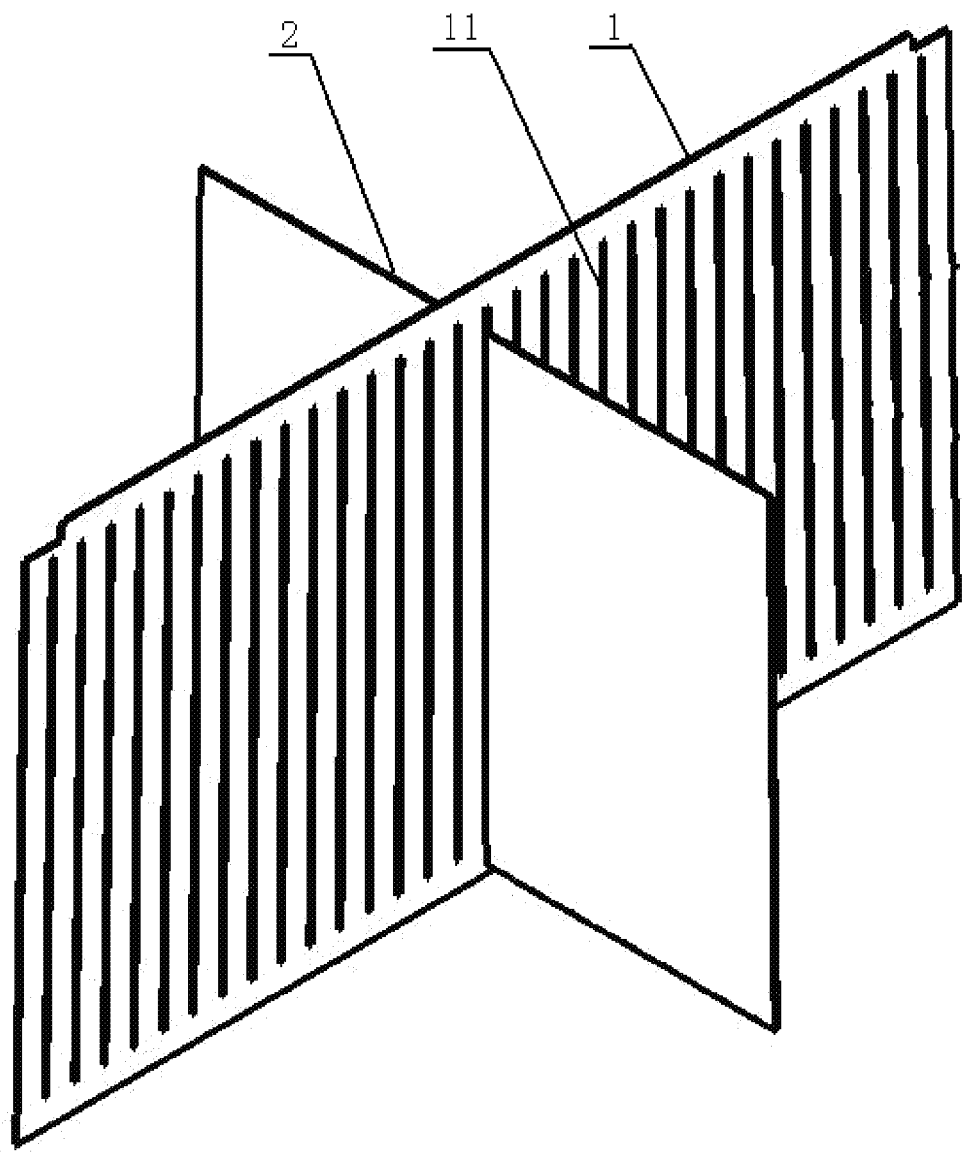
FIG. 7 is a schematic structural perspective view of a first plate and a second plate engaged in a third crossing connection according to the present application.

Referring to FIGS. 6 and 7, FIG. 6 is a schematic structural perspective view of the first plate and the second plate engaged in a second crossing connection according to the present application; and FIG. 7 is a schematic structural perspective view of the first plate and the second plate engaged in a third crossing connection according to the present application.

The first slit 11 may also be provided in the middle of the first plate 1, i.e., the first slit 11 is set to be an enclosed elongated groove, and the height of the first slit 11 may be not smaller than the height of the second plate 2, so that the second plate 2 may be inserted into the first slit 11 in its entirety in the axial direction, as shown in FIGS. 6 and 7.

The middle portion of the first plate 1 means a region that extends from the center of the first plate 1 towards the top end and the bottom end by a certain distance in the vertical direction. That is to say, the middle portion is defined relative to the two ends, not exactly refers to the center portion. In addition, the definition is applicable to any middle portion mentioned herein.

In the second embodiment, the upper end of the second plate 2 may be provided with the second upper slits 22 extending from top towards bottom, so that the second upper slits 22 can receive and be engaged with the upper end of the first plate 1. Then, the upper end of the first slit 11 is positioned and engaged with the second upper slit 22, thereby achieving the positioning of the entire second plate 2.

Also, the lower end of the second plate 2 may be provided with the second lower slits 23. In this way, the second plate 2 is inserted into the first slit 11 in the axial direction, and is pressed downwards such that the second lower slit 23 receives the lower end of the first plate 1. Thus, the lower end of the first slit 11 is positioned and engaged with the second lower slit 23, as shown in FIG. 6.

The cross joints of the first slits 11 and the second upper slits 22 or lower slits 23 may be fixed by adhesive.

Compared with the first slit being open, the enclosed first slit 11 has a higher structural stability, which is not easily deformed, thereby positioning the second plate 2 at a higher precision.

In the third embodiment, the second plate 2 may not be provided with slits. In this case, the second plate 2 may be inserted into the first slit 11 in its entirety in the axial direction, as shown in FIG. 7. Then, the upper end face of the second plate 2 and the upper end face of the first slit 11 are positioned and bonded by adhesive or welding, and the lower end face of the second plate 2 and the lower end face of the first slit 11 are positioned and bonded by adhesive or welding.

Figure 8:
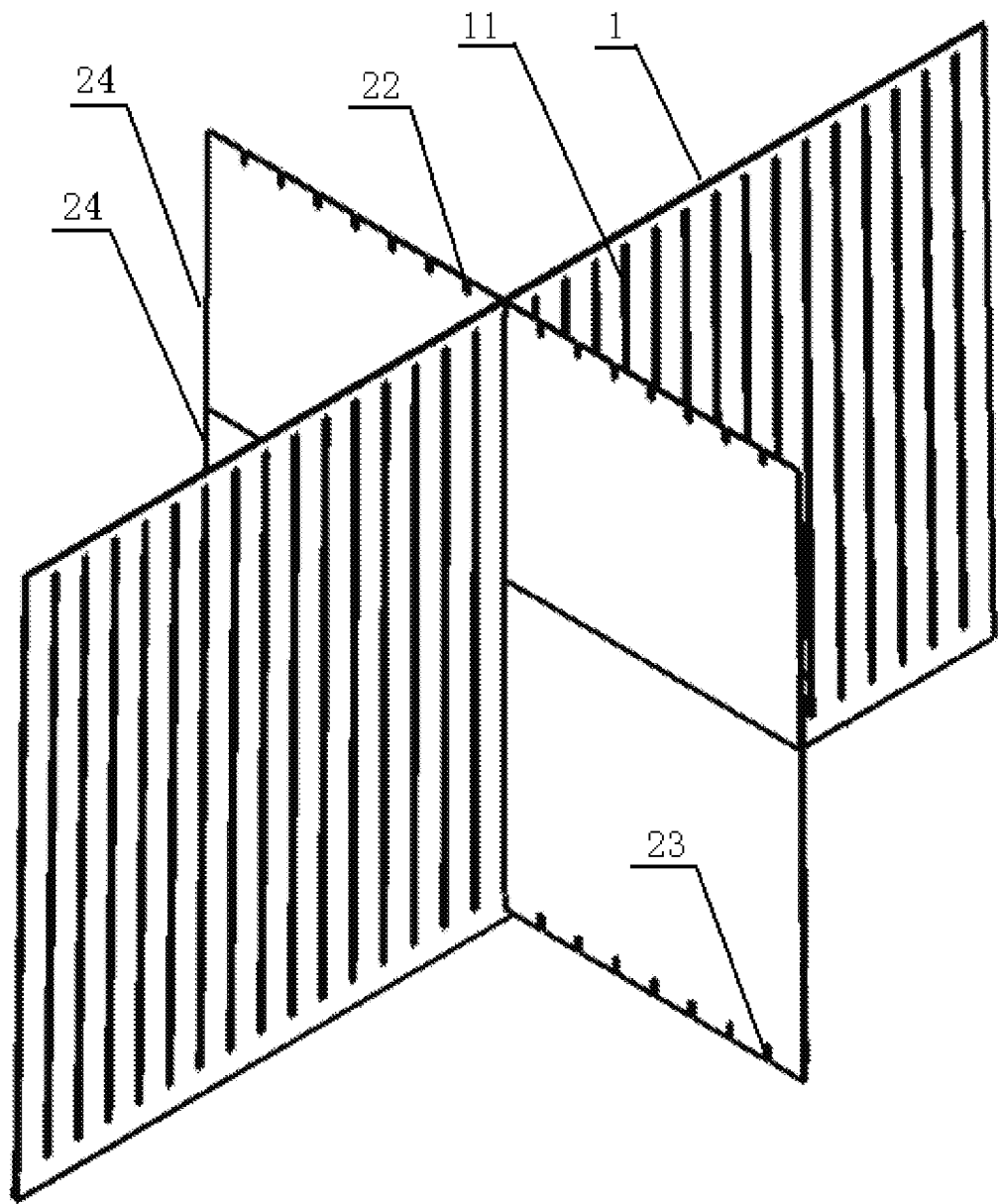
FIG. 8 is a schematic view of a first plate and a second plate engaged in a fourth crossing connection according to the present application.
Figure 9:
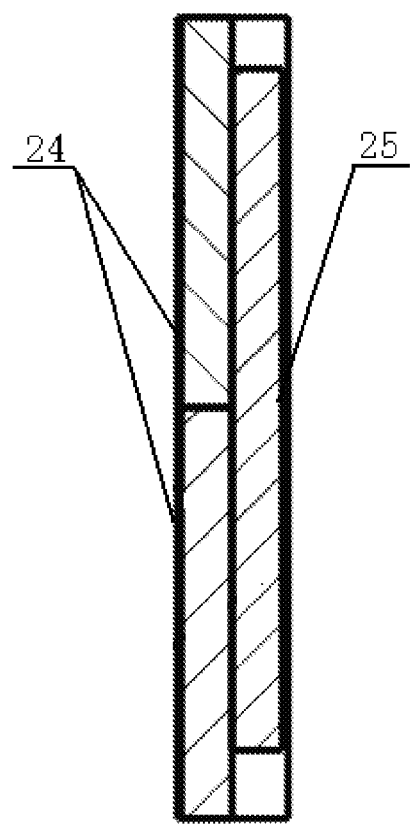
FIG. 9 is a schematic structural sectional view of FIG. 8 with the second plate positioned in the first slit.

Further referring to FIGS. 8 and 9, FIG. 8 is a schematic structural perspective view of the first plate and the second plate engaged in a fourth crossing connection according to the present application; and FIG. 9 is a schematic structural sectional view of FIG. 8 with the second plate positioned in the first slit.

In the fourth embodiment, the second plate 2 may include two or more sub-plates 24 which are stacked in the vertical direction, as shown in FIG. 8. Here, two sub-plates 24 are illustrated by way of example. The top sub-plate 24 may be provided at its upper end with the second upper slits 23, and the bottom sub-plate 24 may be provided at its lower end with the second lower slits 23. Then, the top sub-plate 24 may be positioned by the second upper slits 22 receiving and being engaged with the upper end of the first plate 1, and the bottom sub-plate 24 may be positioned by the second lower slits 23 receiving and being engaged with the lower end of the first plate 1, as shown in FIG. 8.

Besides, the second plate 2 further includes an infill plate 25, which can be adhesively bonded or welded at the back of each sub-plate 24 so that the sub-plates 24 in the vertical direction are connected to form one piece, as shown in FIG. 9. Because the infill plate 25 together with the sub-plates 24 is inserted into the first slit 11, the first slit 11 can be filled, so that the sub-plates 24 are pressed and positioned in the first slit 11, thereby achieving a stable positioning of the first plate 1 and the second plate 2.

Figure 10:
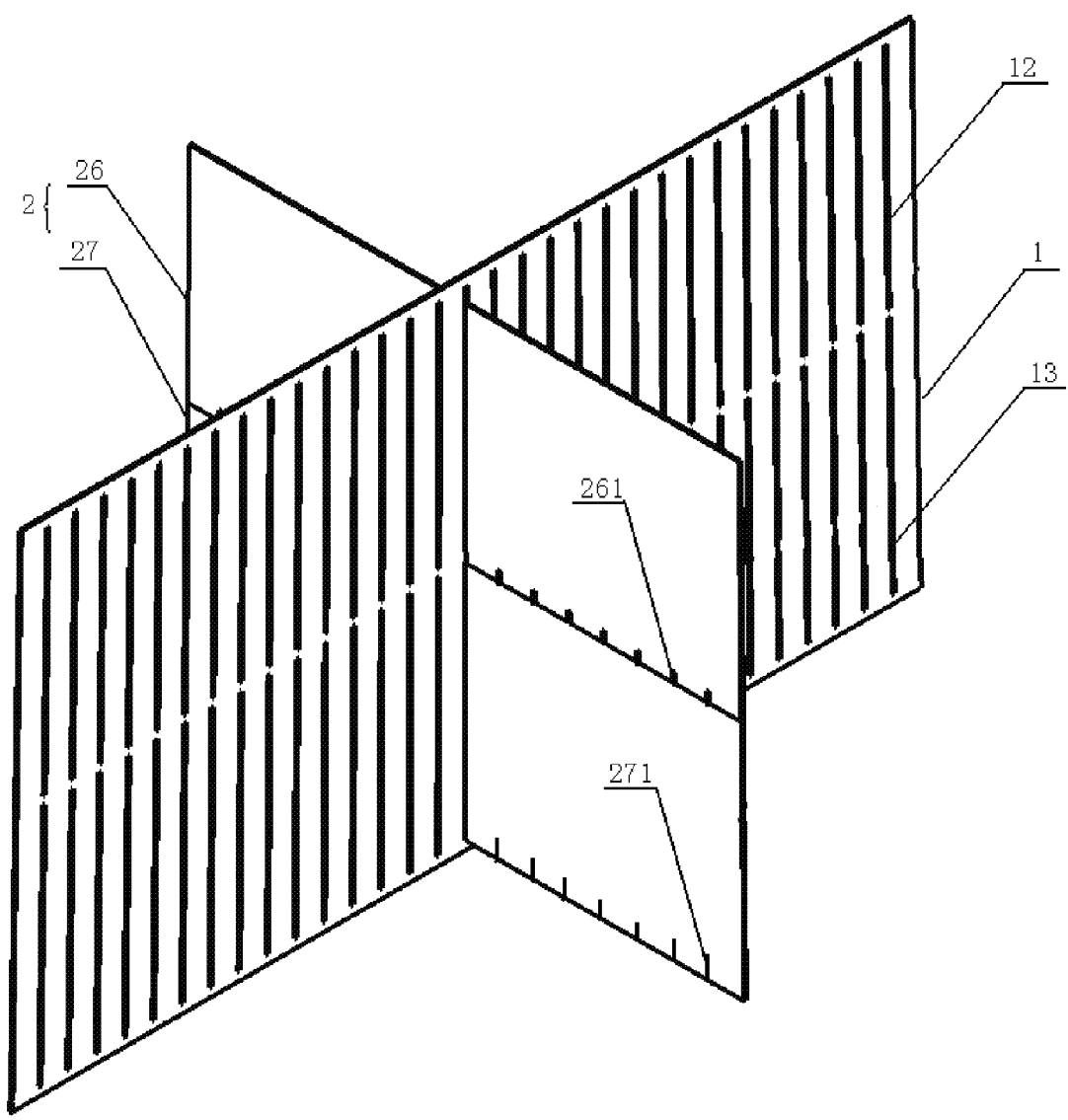
FIG. 10 is a schematic structural perspective view of a first plate and a second plate engaged in fifth crossing connection according to the present application.

Referring to FIG. 10, FIG. 10 is a schematic structural perspective view of the first plate and the second plate engaged in a fifth crossing connection according to the present application.

In the fifth embodiment, the first slit 11 includes a first upper slit 12 and a first lower slit 13. The first upper slit 12 and the first lower slit 13 are spaced apart in the vertical direction. The second plate 2 includes an upper plate 26 and a lower plate 27. The upper plate 26 is inserted and positioned in the first upper slit 12, and the lower plate 27 is inserted and positioned in the first lower slit 13.

To further improve the connecting reliability and reduce the deformation of the first plates 1 and the second plates 2, the first slit may include an upper sub-slit and a lower sub-slit, and correspondingly, the second plate 2 may include an upper plate 26 and a lower plate 27, which may be inserted into the upper sub-slit and the lower sub-slit respectively. Compared with integral first slits 11 and integral second plates 2, the structure in the fifth embodiment is positioned more precisely, forming through holes 3 at a higher precision. Compared with the fourth embodiment, the fifth embodiment omits the infill plate 25, making the assembling process easier.

In the embodiment shown in FIG. 10, the lower end of the upper plate 26 may be provided with the upper plate slits 261, which extend from bottom towards top. Then, the upper plate slit 261 may be inserted and engaged with the lower end of the first upper slit 12.

Further, the lower end of the lower plate 27 may be provided with lower plate slits 271 extending from bottom towards top, so that the lower plate slits 271 and the lower end of the first lower slits 13 are engaged with each other and positioned.

To positioning reliably, the cross joints of the upper plate slits 261 and the first upper slits 12, as well as the cross joints of the lower plate slits 271 and the first lower slits 13, may be bonded or welded to achieve assistant positioning.

Figure 11:
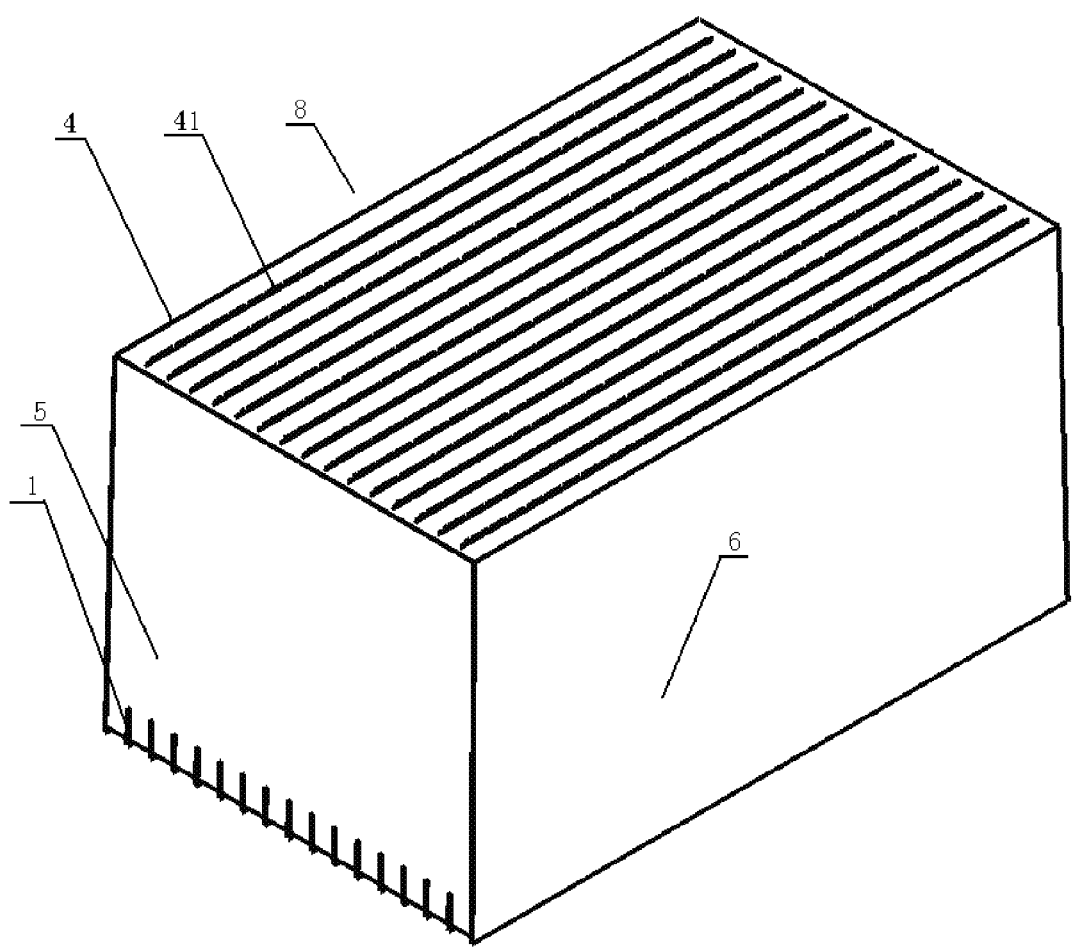
FIG. 11 is a schematic structural perspective view of a X-ray collimator having a positioning plate mounted thereon according to the present application.
Figure 12:
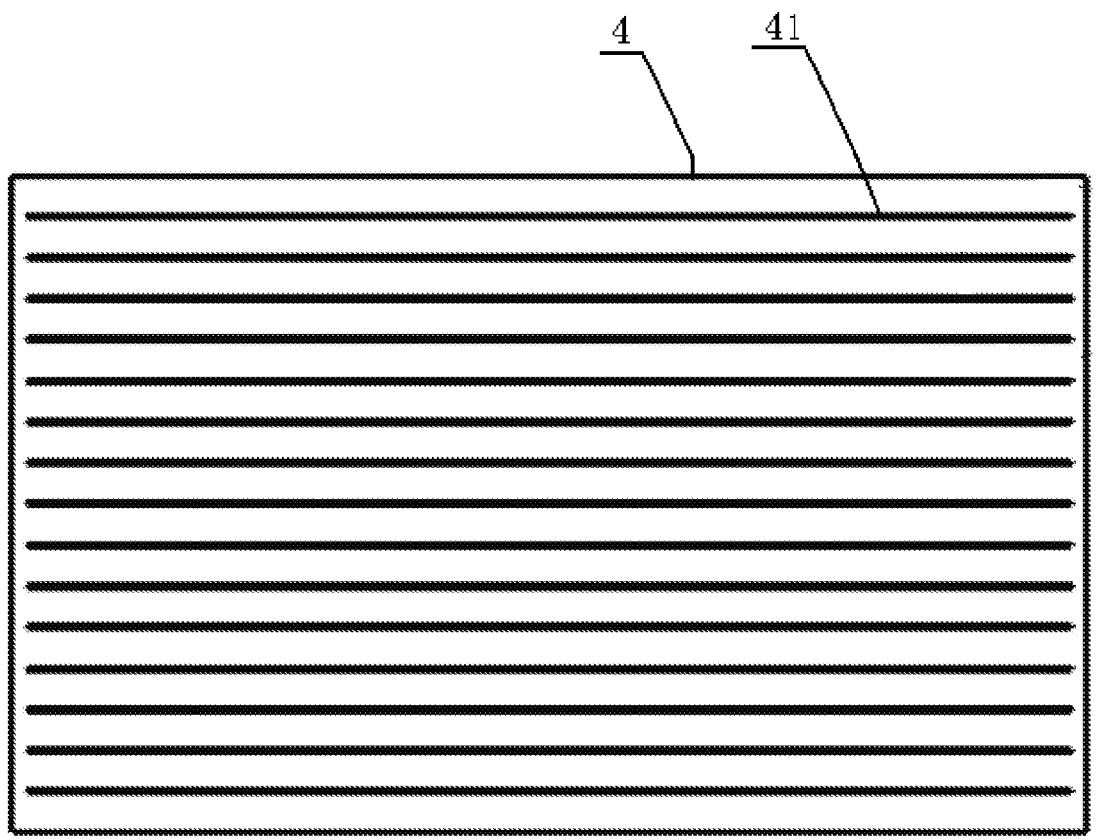
FIG. 12 is a schematic structural view of the positioning plate shown in FIG. 11 in one arrangement.
Figure 13:
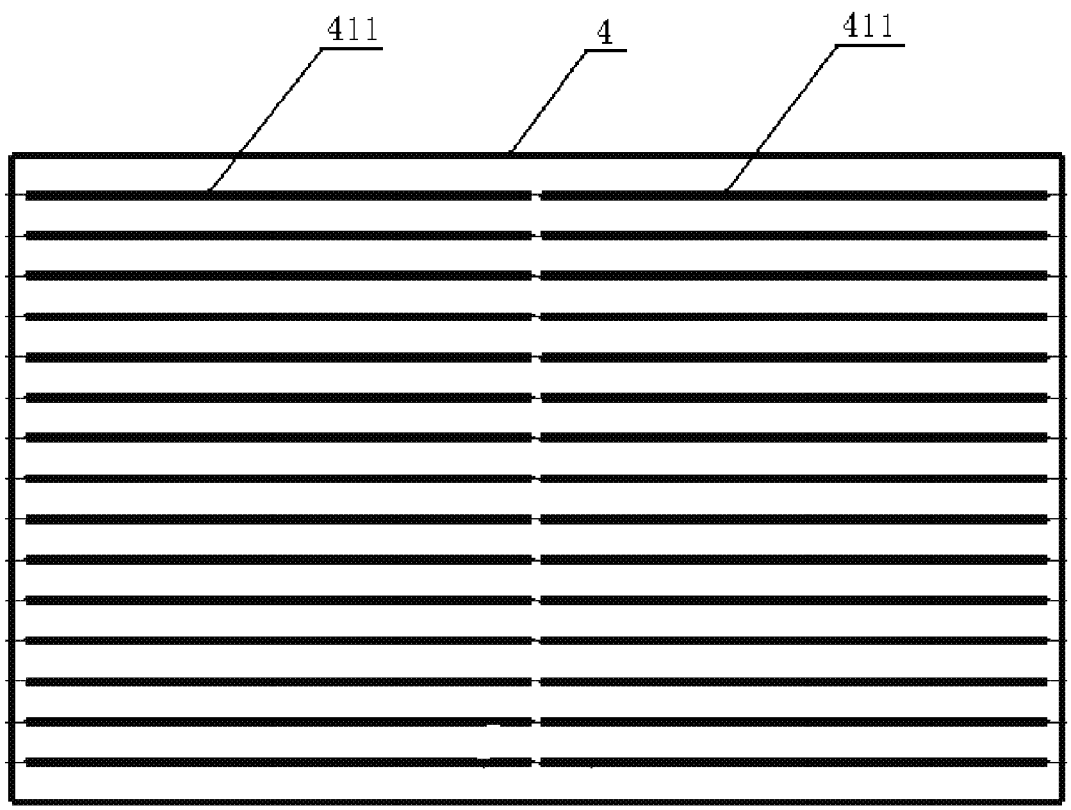
FIG. 13 is a schematic structural view of the positioning plate in another arrangement according to the present application.
Figure 14:
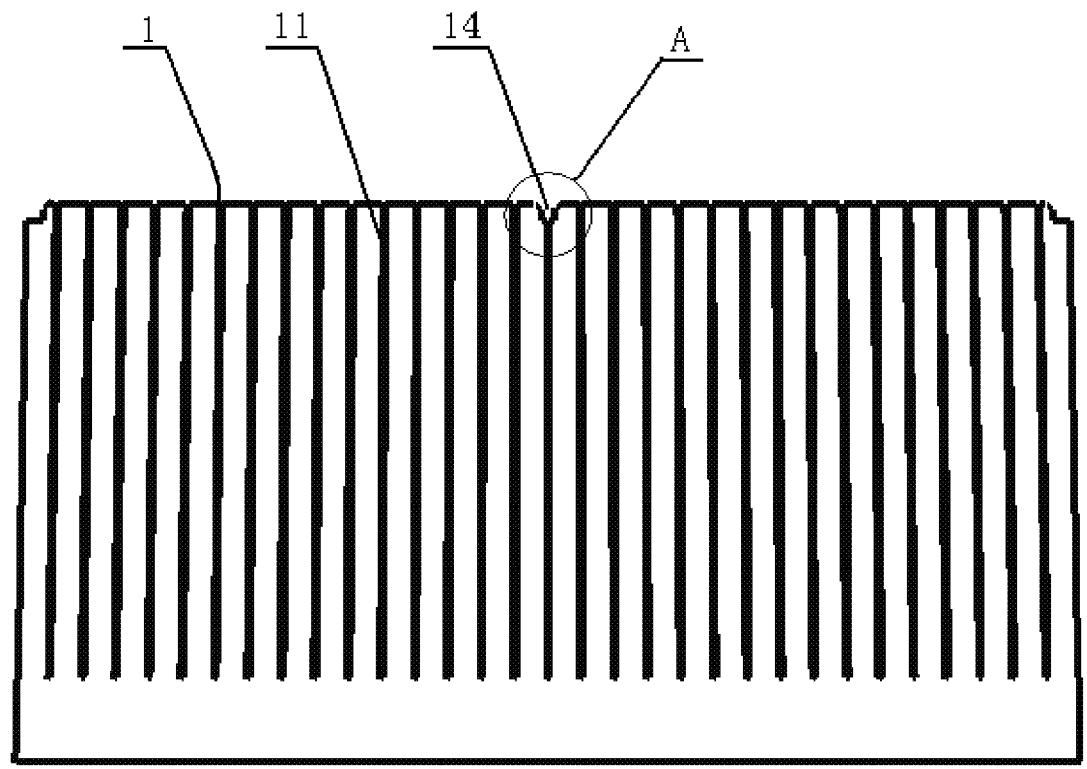
FIG. 14 is a schematic structural view of the first plate in one arrangement according to the present application.
Figure 15:
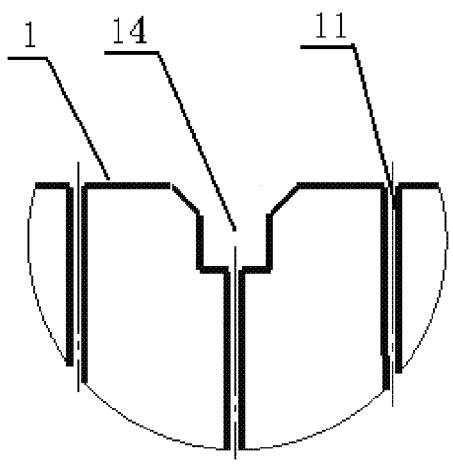
FIG. 15 is a partially enlarged schematic view of part A in FIG. 14.

Referring to FIGS. 11 to 15, FIG. 11 is a schematic structural perspective view of a X-ray collimator having a positioning plate mounted thereon according to the present application; FIG. 12 is a schematic structural view of the positioning plate shown in FIG. 11 in one arrangement; FIG. 13 is a structural schematic view of the positioning plate in another arrangement according to the present application; FIG. 14 is a schematic structural view of the first plate in one arrangement according to the present application; and FIG. 15 is a partially enlarged schematic view of part A in FIG. 14.

Besides, a positioning plate 4 may be further provided in the present application, which may be provided with a plurality of positioning grooves 41 extending in the circumferential direction. The positioning grooves 41 are arranged to be correspond to the first plates 1 respectively. The positioning grooves 41 and the first plates 1 are arranged in the same orientation, such that each of the positioning grooves 41 is engaged with and positioned at the upper end of the corresponding first plate 1.

The positioning plate 4 may achieve the auxiliary positioning of the upper ends of the first plates 1, which improves the assembly convenience of the first plates 1. The function of the positioning plate is similar to the assembling tool having a plurality of positioning grooves as mentioned above. Besides, the positioning plate 4 may serve as a cover plate covering on the top of the first plates 1, which may prevent foreign matters such as dust from falling into the through holes 3 of the X-ray collimator 8, further ensuring a reliable collimating effect.

The positioning plate 4 may be made of material with low X-ray attenuation, for example, organic glass, polycarbonate (PC), PEC, etc. The thickness of the positioning plate 4 may be set between 0.2 mm~1 mm. After the positioning plate 4 is engaged with the upper end of the first plate 1, they may be bonded for assistant positioning.

Because the top sides of the first plates 1 are straight and substantially parallel to each other, the positioning grooves 41 may be straight and parallel to each other, as shown in FIG. 12.

It can be conceived that the positioning grooves 41 may be configured as run-through grooves or blind grooves on the underside of the positioning plate 4. The positioning plate 4 may be processed by mechanical engraving or laser cutting to form the positioning grooves 41.

As shown in FIGS. 13 to 15, the positioning groove 41 may include two or more sub-grooves 411 spaced-apart in the circumferential direction. The solid portion between two adjacent sub-grooves 411 is set to have a predetermined width. The predetermined width is much smaller than the smallest value of the lengths of the positioning grooves 41. The predetermined width refers to a size in the circumferential direction.

For this, the upper end of the first plate 1 may be provided with a notch 14, as shown in FIGS. 14 and 15. The notch 14 is provided at a place corresponding to the solid portion between the two adjacent sub-grooves 411, so as to accommodate the solid portion, making the positioning plate 4 in a good contact with the first plate 1 and ensuring a reliable connection therebetween. Since the notch 14 has a height much lower than that of the first plate 1 and has a small length in the circumferential direction, the notch 14 has little effect on the uniformity of the pixels. Thus, the collimating unit for each pixel may be regarded as being uniform.

It will be appreciated that, although the positioning grooves 41 may include a plurality of sub-grooves 411 to improve the structural stability of the positioning plate 4 and effectively position the first plate 1, the uniformity of collimation effect may be affected if there are too many notches 14. Thus, the number of the sub-grooves 411 should be limited, and generally, two or three sub-grooves are preferable.

As shown in FIGS. 2 and 11, first guard plates 5 and second guard plates 6 may be further provided in the present application. The first guard plates 5 are provided at opposite ends of the first plate 1, and the second guard plates 6 are provided at opposite ends of the second plate 2. Thus, the first guard plates 5 enclose the both ends of each of the first plates 1, and the second guard plates 6 enclose the both ends of each of the second plates 2. The both ends of the first plate 1 and the both ends of the second plate 2 refer to the two ends in the respective extending direction of them.

The thickness of the first guard plate 5 and the second guard plate 6 can be set. For example, the thickness of the first guard plate 5 may be substantially half of the thickness of the second plate 2, and the thickness of the second guard plate 6 may be substantially half of the thickness of the first plate 1.

The wording "substantially" herein includes the meaning of "equal to" and a small deviation. The deviation means that the thickness of the plate formed by joining the two first guard plates 5 or the two second guard plates 6 can meet the requirement of thickness of walls of the through hole 3, i.e., it will not block the X-ray.

When joining the two collimators 8 together, the first guard 5 may be joined with another first guard plate 5 of the adjacent X-ray collimator 8 to form a plate with the thickness substantially equal to a second plate, which is engaged with the first plate 1 to define through holes 3 meeting the requirement of collimation. Similarly, the second guard plate 6 may also be joined another adjacent second guard plate 6 so as to join the two or more X-ray collimators 8 one by one to form a large X-ray collimator, i.e., a larger shielding layer.

Figure 17:
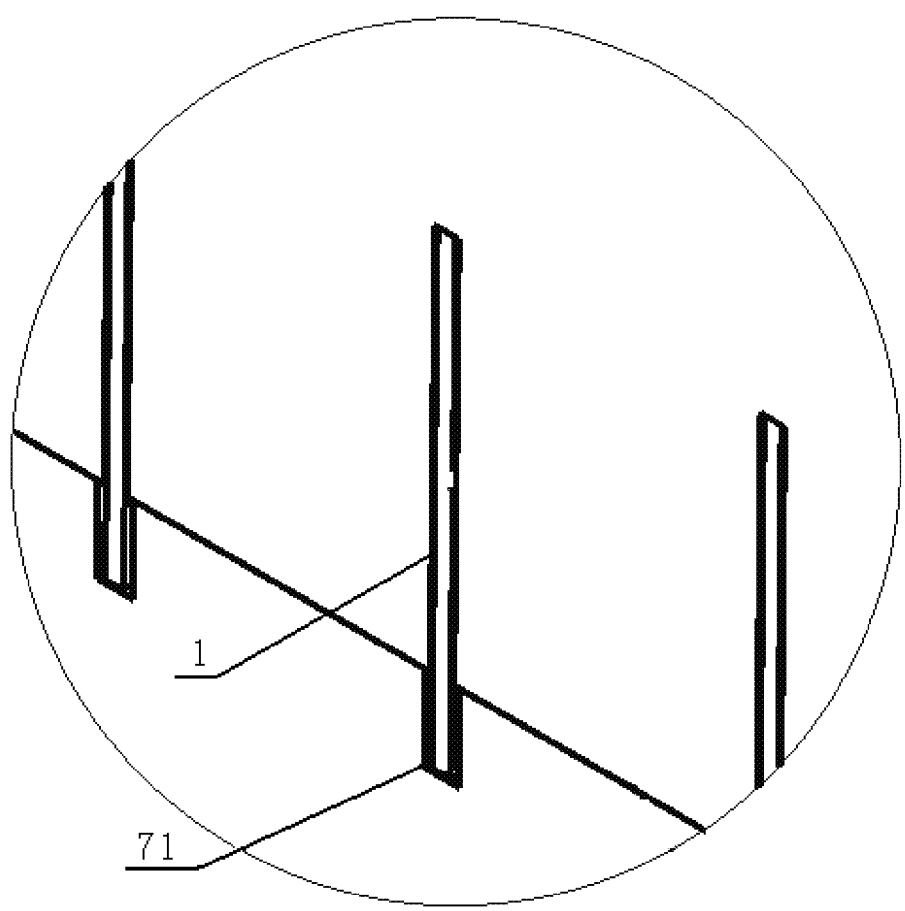
FIG. 17 is a partially enlarged schematic view of part B in FIG. 16.

With reference to FIGS. 16 and 17, FIG. 16 is a schematic structural perspective view of the X-ray collimator in FIG. 2 mounted on the X-ray detector; and FIG. 17 is a partially enlarged schematic view of part B in FIG. 16.

There is further provided a computed tomography system in the present application. The computed tomography system includes an X-ray detector 7 and an X-ray collimator 8 for collimating the X-rays radiating to the X-ray detector 7. The X-ray collimator 8 may be any one of the above mentioned X-ray collimators 8. For other structures of the computed tomography system, please refer to the conventional computed tomography system in the prior art, which are not described here.

Specifically, as shown in FIGS. 16 and 17, the X-ray collimator 8 is mounted on the X-ray detector 7, such that each through hole 3 of the X-ray collimator 8 corresponds to a detecting unit of the X-ray detector 7. A plurality of partition grooves 71 are provided in partition regions between the pixels of the X-ray detector 7, and the lower ends of the first plates 1 of the X-ray collimator 8 are embedded into the partition grooves 71, thereby assembling and positioning the X-ray collimator 8 and the X-ray detector 7.

A detailed description has been made to the computed tomography system and the X-ray collimator thereof according to the present application. The principle and the embodiments of the invention have been illustrated by way of examples, and the above description of the embodiments is provided only for better understanding the concept of the invention. It should be noted that those skilled in the art may make many improvements or modifications to these embodiments without departing from the spirit or scope of the present application. These improvements or modifications will fall into the scope of protection as defined in Claims.

The invention claimed is:

1. An X-ray collimator of a computed tomography system, wherein the X-ray collimator comprises a plurality of first plates extending in the circumferential direction of the computed tomography system and a plurality of second plates extending in the axial direction of the computed tomography system; the first plates and the second plates are inserted and engaged with each other; each of the first plates is provided with a plurality of first slits spaced apart in a circumferential direction, and each of the second plates is provided with a plurality of second slits spaced apart in an axial direction, the height of the first slit is larger than half of the entire height of the first plate or the height of the second slit is larger than half of the entire height of the second plate, and two adjacent first plates and two adjacent second plates define a through hole, and extensions of all of side walls of the through hole intersect at a focal spot of an X-ray source, so that X-rays can pass through the through hole in a straight line;

wherein the X-ray collimator further comprises a positioning plate, the positioning plate is provided with a plurality of positioning grooves extending in the circumferential direction, and each of the positioning grooves is engaged with and positioned relative to an upper end of a corresponding first plate for further positioning;

each of the positioning grooves is a run-through groove; and each of the positioning grooves comprises two or more sub-grooves spaced apart in the circumferential direction, and a solid portion between two adjacent sub-grooves is set to have a predetermined width, and the upper end of each first plate is provided with a notch for accommodating the solid portion.

2. The X-ray collimator according to claim 1, wherein the cross joints of the first slits and the second slits are positioned by adhesive bonding or welding.

3. The X-ray collimator according to claim 1, wherein a first guard plate is provided at each of two ends of each first plate, and a second guard plate is provided at each of two ends of each second plate, and the first guard plates and the second guard plates enclose the ends of the first plates and the second plates respectively.

4. The X-ray collimator according to claim 3, wherein the thickness of the first guard plate is substantially half of the thickness of the second plate, and the thickness of the second guard plate is substantially half of the thickness of the first plate.

5. A computed tomography system, comprising an X-ray detector and an X-ray collimator for collimating X-rays radiating to the X-ray detector, wherein the X-ray collimator comprises a plurality of first plates extending in a circumferential direction of the computed tomography system and a plurality of second plates extending in an axial direction of the computed tomography system; the first plates and the second plates are inserted and engaged; each of the first plates is provided with a plurality of first slits spaced apart in the circumferential direction, and each of the second plates is provided with a plurality of second slits spaced apart in the axial direction, the height of the first slit is larger than half of the entire height of the first plate; or the height of the second slit is larger than half of the entire height of the second plate, two adjacent first plates and two adjacent second plates define a through hole, and extensions of all of side walls of the through hole intersect at a focal spot of an X-ray source, so that X-rays can pass through the through hole in a straight line;

wherein the X-ray collimator further comprises a positioning plate, the positioning plate is provided with a plurality of positioning grooves extending in the circumferential direction, and each of the positioning grooves is engaged with and positioned relative to an upper end of a corresponding first plate for further positioning;

each of the positioning grooves is a run-through groove; and each of the positioning grooves comprises two or more sub-grooves spaced apart in the circumferential direction, and a solid portion between two adjacent sub-grooves is set to have a predetermined width, and the upper end of each first plate is provided with a notch for accommodating the solid portion.

6. The computed tomography system according to claim 5, wherein the X-ray collimator is mounted on the X-ray detector, and each through hole corresponds to a detecting unit of the X-ray detector; a plurality of partition grooves are provided in partition regions between pixels of the X-ray detector, and the lower end of the first plate is embedded into the partition groove.

7. The X-ray collimator according to claim 1, wherein the height of the first slit is lower than 5 mm or the height of the second slit is lower than 5 mm.

8. The computed tomography system according to claim 5, wherein the height of the first slit is lower than 5 mm or the height of the second slit is lower than 5 mm.

* * * * *